United States Patent
Kotchou et al.

(10) Patent No.: US 9,058,648 B2
(45) Date of Patent: Jun. 16, 2015

(54) IMAGE ACQUISITION FOR CHEMILUMINESCENT SAMPLES

(71) Applicant: Bio-Rad Laboratories, Inc., Hercules, CA (US)

(72) Inventors: Keith Kotchou, Walnut Creek, CA (US); Kevin McDonald, Novato, CA (US); James Lee, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 287 days.

(21) Appl. No.: 13/803,562

(22) Filed: Mar. 14, 2013

(65) Prior Publication Data

US 2013/0243283 A1    Sep. 19, 2013

Related U.S. Application Data

(60) Provisional application No. 61/611,293, filed on Mar. 15, 2012.

(51) Int. Cl.
*G06K 9/00* (2006.01)
*G06T 7/00* (2006.01)
*G01N 21/76* (2006.01)
*G06T 5/00* (2006.01)
*G06T 5/50* (2006.01)
*H04N 5/235* (2006.01)

(52) U.S. Cl.
CPC ..... *G06T 7/0012* (2013.01); *G06T 2207/10064* (2013.01); *G01N 21/76* (2013.01); *G06T 5/008* (2013.01); *G06T 5/50* (2013.01); *H04N 5/2355* (2013.01); *G06T 2200/21* (2013.01); *G06T 2207/10144* (2013.01); *G06T 2207/20012* (2013.01); *G06T 2207/20208* (2013.01); *G06T 2207/30004* (2013.01); *H04N 5/2351* (2013.01)

(58) Field of Classification Search
CPC .................... G01N 21/76; G06T 2207/10064; G06T 2207/10144
USPC .......................................................... 382/128
See application file for complete search history.

(56) References Cited

U.S. PATENT DOCUMENTS

| | | | | |
|---|---|---|---|---|
| 5,625,415 | A * | 4/1997 | Ueno et al. | 348/350 |
| 6,791,618 | B1 | 9/2004 | Shimizu | |
| 7,687,239 | B2 * | 3/2010 | Goldberg et al. | 435/7.2 |
| 7,920,733 | B2 * | 4/2011 | Matsuo et al. | 382/129 |

(Continued)

FOREIGN PATENT DOCUMENTS

WO    94/25855    11/1994

OTHER PUBLICATIONS

International Search Report of PCT/US2013/031626 mailed on Mar. 14, 2013, 51 pages.

*Primary Examiner* — Utpal Shah
(74) *Attorney, Agent, or Firm* — Kilpatrick Townsend & Stockton LLP

(57) ABSTRACT

An image system for detecting chemiluminescence in a sample uses a highly binned, short exposure initial image to calculate the exposure time for a final image of the sample. After calculation of the exposure time, at least two final images are taken, with saturated pixels removed and replaced in a first image with corresponding unsaturated pixels from a second image. The corresponding pixels are adjusted to reflect the different intensity levels between the first and second images, and the first image becomes the final image reflecting the detected chemiluminescence.

21 Claims, 3 Drawing Sheets

(56) References Cited

U.S. PATENT DOCUMENTS

| | | |
|---|---|---|
| 2003/0170613 A1 | 9/2003 | Straus |
| 2004/0101912 A1 | 5/2004 | Rubin et al. |
| 2006/0031019 A1 | 2/2006 | Staton et al. |
| 2008/0075380 A1* | 3/2008 | Dube et al. ............... 382/255 |
| 2009/0161929 A1* | 6/2009 | Oba et al. ............... 382/128 |
| 2010/0025588 A1 | 2/2010 | Trupke et al. |
| 2010/0056928 A1 | 3/2010 | Zuzak et al. |
| 2010/0248387 A1 | 9/2010 | Gambini et al. |
| 2011/0203924 A1 | 8/2011 | Wohlstadter et al. |
| 2011/0305388 A1 | 12/2011 | Wedi et al. |
| 2013/0034284 A1* | 2/2013 | Honkanen et al. ............ 382/129 |
| 2014/0009603 A1* | 1/2014 | Atkin et al. ............... 348/135 |

\* cited by examiner

IMAGE ACQUISITION FOR CHEMILUMINESCENT SAMPLES

This application claims the benefit of and is a non-provisional of U.S. Application Ser. No. 61/611,293, filed on Mar. 15, 2012, which is incorporated by reference in its entirety for all purposes.

BACKGROUND OF THE INVENTION

Imaging systems use luminescence to detect the presence of proteins, nucleic acids and other biological substances. Measuring the intensity of the luminescence will provide an indication of the concentration of the substance in a sample, for example, by comparing the intensity of the light among a plurality of samples or sample spots on a substrate.

When the luminescence is the result of excitation of the sample by an external excitation source (e.g., a light source), the luminescence or emission of light will typically be constant, and a useful dynamic range of detected light levels for comparing intensities can usually be obtained without difficulty.

In some cases, chemiluminescence may be a preferred technique for the detection of certain substances. In chemiluminescense, light is emitted from a sample based on a chemical reaction, resulting, for example, from the introduction of an enzyme and an oxidant to a sample of a protein or other substance of interest.

One limitation of chemiluminescence is that the emitted light tends to be faint, and it has a limited half-life and it degrades over time. As a result, it can be difficult to accurately determine the exposure time needed to get the best measurement of emitted light in an image that will provide a useful dynamic range of light levels. When using a photo detector device (such as a CCD camera), the exposure time should provide a dynamic range of light levels that capture enough light from sample spots giving off the lowest light intensity for meaningful evaluation, but without other spots emitting too much light and resulting in individual CCD elements becoming saturated due to over exposure. In the past, the exposure time of a chemiluminescent sample was often the result of a somewhat subjective estimate. The estimated exposure time does not always provided a good result and multiple measurements might need to be taken to obtain useful data.

BRIEF SUMMARY OF THE INVENTION

There is provided, in accordance with embodiments of the present invention, a system and method for detecting chemiluminescence from samples. An exposure time is calculated for an image in order to capture light signals. In one embodiment, the calculation of exposure time is based on a highly binned initial image. In another embodiment, a final image having detected or captured light is obtained from two final images, namely, a first final image acquired using the calculated exposure time, and a second final image having a shorter exposure time in order to avoid saturated pixels. Saturated pixels in the first image are replaced with corresponding unsaturated pixels from the second final image, to arrive at the final image representing the detected light from chemiluminescence.

In yet another embodiment there is provided a method for measuring the chemiluminescence of a sample. The method includes acquiring a binned initial image of the sample, the initial image having a first binning value representing the number of pixel elements in its image pixels; and calculating an exposure time for a final image of the sample, the final image having a second binning value representing the number of pixel elements in its image pixels, wherein the first binning value is larger than the second binning value, and wherein the calculation is based on a pixel ratio of the first binning value to the second binning value. The method further includes acquiring at least first and second final images of the sample, wherein the first final image is acquired using the calculated exposure time, wherein the second final image is acquired using an exposure time shorter than the calculated exposure time; and identifying pixels in the first final image that are saturated. The method further includes measuring the intensity of luminescence of corresponding features in both the first and second final images, wherein measuring provides an intensity ratio that reflects the intensity of features in the first final image in relation to the intensity of the corresponding features in the second final image; substituting, for any saturated pixels in the first final image, corresponding unsaturated pixels from the second final image; and adjusting the intensity of the corresponding pixels that have been substituted for saturated pixels according to the intensity ratio.

A more complete understanding of the present invention may be derived by referring to the detailed description of the invention and to the claims, when considered in connection with the Figures.

DETAILED DESCRIPTION OF THE INVENTION

Figure 1:
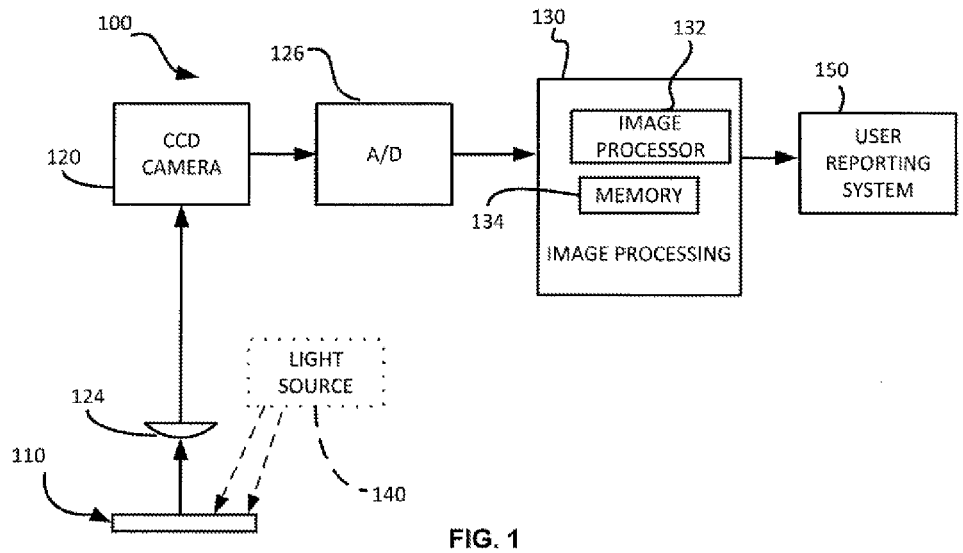
FIG. 1 is a simplified block diagram of an imaging system in accordance with an embodiment of the invention.

There are various embodiments and configurations for implementing the present invention. Generally, embodiments provide systems and methods for detecting chemiluminescence of biological substances, such as protein samples, based on the presence (in a captured image) of luminescence or light emitted from a sample. An exposure time is calculated for an image where the intensity of light from chemiluminescence represents the concentration of the substance being detected. In one broad aspect of the invention, the calculation of exposure time is based on highly binned (and thus lower resolution) initial image. In another broad aspect of the invention, a final image representing detected or captured light is obtained from a first final image acquired using the calculated exposure time, and a second final image having a shorter exposure time to avoid saturated pixels. Saturated pixels in the first image are replaced with corresponding unsaturated pixels from the second final image, to arrive at the final image representing the detected light from chemiluminescence.

In one embodiment, the exposure time for detecting light signals emitted from a sample is calculated by acquiring an initial image at a CCD (charge coupled device) camera that is highly binned and thus has low resolution. Binning is a known technique for combining a number of camera (CCD) pixel elements into a single image pixel. Binning permits a shorter exposure time to capture data, having lower resolution but reduced noise level. Thus a highly binned initial image can be used for calculating exposure time for a final sample image by quickly detecting a range of light intensities emitted from the sample (including the highest intensity light that may result in pixel saturation), before the chemiluminescent sample will significantly degrade.

Generally, the highly binned initial image will be used to calculate the exposure time for a final image by using the initial data to determine when the highest intensity signals would reach saturation in a final image. As an example, in one implementation, the highly binned image is set at a binning value of 16×16, i.e., 256 CCD pixel elements or cells are combined into a single image pixel. Such a highly binned image permits a much shorter exposure time to measure light intensity and, although of lower resolution, the highly binned image results in a higher signal-to-noise ratio. The initial image is measured or examined for saturated pixels (e.g., if pixel data values are each represented by sixteen bits and thus can be any value in a range from 0 to 65,535, then saturated pixels are those pixels having a value at 65,535). If any pixels are saturated, then a second initial image is acquired using a reduced exposure time. In one implementation, the second initial image would have an exposure time that is one-third the exposure time of the first initial image.

The initial image may also be measured for sufficient light signals above noise level of the photo detection system (CCD camera). For example, a CCD camera will emit a normal, small level noise signal from its pixel cells. There must be a sufficient number of pixels that are emitting signals above the noise level to be assured that there is enough data to predict when the highest intensity signals will reach or be sufficiently close to saturation. In one exemplary embodiment, 0.1% of pixels in the initial image should be at or above 12.5% of full dynamic range (although it should be appreciated that other threshold percentages could be chosen, depending on the design of the system).

In the described embodiment, once an initial image is found acceptable, then the exposure time for a final image of the same sample is calculated. The calculation may be based on the pixel ratio of the binning value used in the initial image to the binning value used for the final image, i.e., the ratio of the number of pixel elements in each initial image pixel to the number of pixel elements in each final image pixel. In one exemplary embodiment herein, the initial image is set to be binned at 16×16 (256 pixel elements per image pixel), and the final image is set to be binned at 4×4 (16 pixel elements per image pixel). In this embodiment, the pixel ratio is sixteen, and the calculated exposure time is established as being sixteen times the exposure time of the initial image (i.e., each binned image pixel in the final image is $\frac{1}{16}$ the size of the binned image pixels in the initial image, and thus would require sixteen times the exposure to get a corresponding image). It should be appreciated that the foregoing binning sizes for the initial and final images are only exemplary, and could be different, as long as the binning for the initial image (used for calculating the final exposure time) is larger than for the final image. In the case of the final image, the binning size will usually be established by the user based on the degree of resolution desired (and in some case there might be no binning at all, i.e., each image pixel will be 1×1).

A first final image of the sample is then taken based on the calculated exposure time. It is expected that at least some of the pixels in the final image will be saturated, since in the described embodiment, the exposure time for the final image is calculated so the highest intensity pixels will reach saturation (or approximate saturation). Thus, a second final image will be acquired (to reduce the likelihood of saturated pixels).

In the described embodiment, the second final image is taken using a reduced exposure time. In one embodiment, the exposure time is reduced by 67% relative to the first final image (although as should be appreciated, other reductions in exposure time for the second image are possible, depending on the design of the system).

It is expected that, in most cases, the second final image would have no saturated pixels, and thus it is stored for further processing along with the first final image. In some embodiments, the second final image is evaluated for saturated pixels, and if found, yet another image is acquired or captured (with a further reduced exposure time) and becomes the second final image. The intended result is that there will be two final images, one with saturated pixels and one without saturated pixels.

As will be described in more detail later, non-saturated pixels (representing image features) in the first final image are identified, and the intensity ratio between those pixels (or image features) in the first final image are compared to the corresponding pixels in the second final image. The saturated pixels in the first final image are replaced with the corresponding pixels in the second final image, with the replacing pixels adjusted upwardly according to the intensity ratio. For example, if the non-saturated pixels in the first final image are 3 times brighter or more intense than the non-saturated pixels in the second final image, the replacing or substitute pixels from the second images have their light intensity increased by 3 times when placed in the first image. Thus, the modified first final image is used as the ultimate final image of measured light or luminescence from the sample, having an extended dynamic range of light levels, from the lowest intensity pixel signals to the highest intensity pixel signals (with the highest intensity pixel signals in the final image having been taken from the second image to avoid having those pixels being over saturated).

Turning now to FIG. 1, there is illustrated a simplified view of an imaging system 100 for analyzing a sample 110 based on light emitted from the sample 110. Typically, the sample 110 will include a substrate on which an array of sample spots are located, each sample spot representing a substance of interest (such as a protein), and having varying degrees of concentration between sample spots (in order to permit comparisons between sample spots). In order to determine the light emitted from the sample, the system 100 includes a CCD camera 120 for receiving the emitted light through a lens 124. The light received by the CCD pixel elements in the camera 120 are provided to an image processing system 130 through an analog-to-digital (A/D) converter 126 (the A/D converter converts the analog signal from the CCD elements in camera 120 to digital signals representing the value or intensity of the detected light). The processing system 130 includes an image processor 132 for processing the digitized signals representing light detected at the CCD camera, and one or more memory devices 134 for storing images as well as software used by the processor 130 in processing and analyzing the images. The system 100 may also include an optional light source 140 for use if the sample 110 requires a light source in order to emit luminescence. However, embodiments of the present invention are generally directed to detecting chemiluminescence where no external source is required.

The imaging system 100 as thus far described is conventional, and could be implemented, for example, by the Chem-Doc MP System available from Bio-Rad Laboratories, Inc., Hercules, Calif. Such a system permits detection of light resulting from excitation of a sample by a light source (such as light source 140) as well as the detection of light resulting from chemiluminescence at the sample 110.

Also seen in FIG. 1 is a user reporting system 150, such as a lap top or desktop personal computer. The reporting system 150 would have a display for illustrating the pattern of light from the sample as detected by camera 120.

Figure 2:
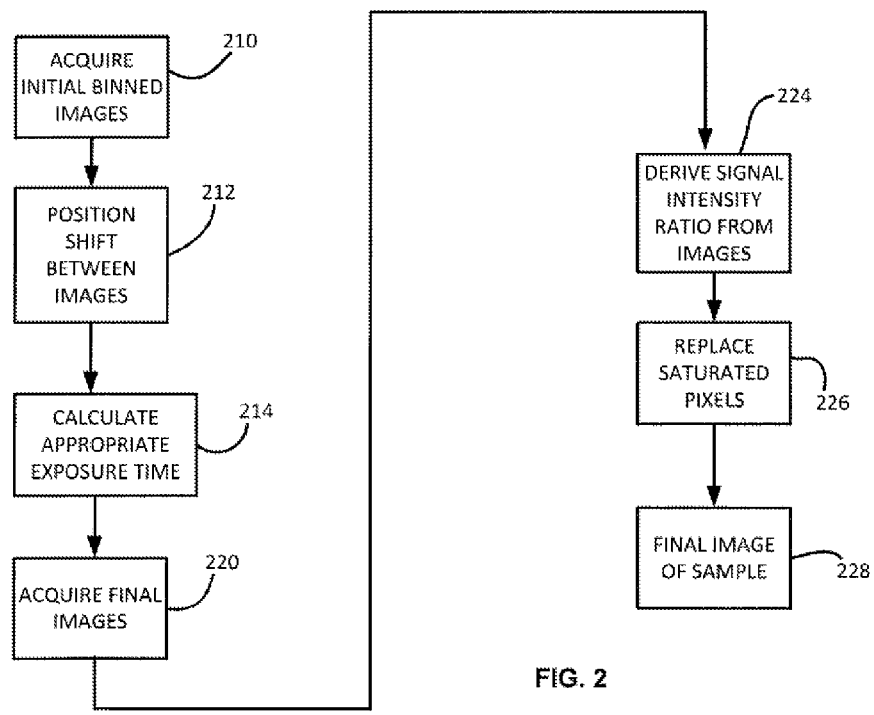
FIG. 2 illustrates a simplified flow diagram of a process, in accordance with one embodiment, for calculating an exposure time and obtaining an image of detected chemiluminescence using the imaging system of FIG. 1.

FIG. 2 illustrates a simplified flow diagram of a process, in accordance with one embodiment, for calculating an exposure time and obtaining a final image of a chemiluminescent sample based on that calculated exposure time. In order to achieve a desirable dynamic range of light signals, the final image exposure time will be calculated so that the pixels for the highest intensity signals will be at or near saturation.

At step 210 one or more initial images are acquired. As mentioned above, the initial images are highly binned (relative to a final image of the sample). Thus, there is a short exposure time (relative to the final image). The exposure time is chosen for at least some of the pixels in the initial image to be right at saturation (or close to saturation). In one implementation, a four second exposure is chosen, but such initial exposure may vary, depending on the design of camera 120. As will be described in greater detail later, multiple initial images may be needed. For example, if any pixels are saturated in the initial image, then the exposure time is reduced and a second initial image is acquired and used for the calculation of the final exposure time. If the signals are not sufficiently above background noise to predict saturation time for the final image, then the exposure time is increased and an image having the increased exposure time is used as the initial image for the calculation of the final exposure time.

In one implementation, once the desired exposure time for the initial image is achieved, an additional image is acquired (step 212) that is displaced (relative to the sample) from the other current initial image. This additional image will detect any higher intensity signals that may straddle two binned image pixels or pixel areas and result in lower intensity light spread across two image pixels. If the additional image has an increased intensity, then the additional image is selected for the final exposure calculation (if not, then the previous image is used as the selected initial image for final exposure calculation). In one implementation, the displacement is half the distance along the x and y axes of the binned image pixel, in order to shift the image by one quadrant in the binned image pixel or pixel area.

At step 214, the exposure time for the final image of the sample is calculated from the selected highly binned initial image. In one embodiment, this calculation involves two separate factors. First, a multiplying factor will be calculated that would bring pixels representing the highest intensity signals in the initial image to saturation. For example, if the highest intensity signals in the selected initial image are at 75% of saturation, then the multiplying factor will be 133% (33% of additional exposure is needed to get to saturation), and thus exposure time of the initial image is multiplied by that multiplying factor. The second factor in calculating the final exposure time is the pixel ratio of the binned initial image pixel size to the final image pixel size. As an example discussed earlier, if the image pixel size (binning value) in the initial image is 16 times larger than the image pixel size in the final image (e.g., if the initial image is binned at 16×16, and the final image is binned at 4×4), then the final exposure time is increased by 16, i.e., the exposure time of the initial image is increased by multiplying it by the pixel ratio of 16 (in addition to any multiplying factor needed to reach saturation).

At step 220, multiple final images are acquired in order to arrive at a single final image (i.e., data values for each pixel in the single final image) that will represent the detected chemiluminescence of the sample. A first final image is acquired using the exposure time calculated at step 214. Then a second final image is acquired with a reduced exposure time (in one implementation, the exposure time is reduced to 33% of the exposure time of the final image). Thus, in most instances, the second final image will have no saturated pixels. Acquiring two images permits the ultimate final image to have an extended dynamic range of light levels or intensities. In particular, a signal intensity ratio is obtained by comparing non-saturated pixels or features in first final image to the same pixels in the second final image, at step 224. The comparison yields a signal intensity ratio. As an example only (for purposes of illustration), if the average intensity of non-saturated pixels in first final image is twice the intensity of the corresponding pixels in the second final image, the signal intensity ratio is two. The actual signal intensity ratio will, of course, vary depending (among other things) on exposure times of the first and second final images.

At step 226, the saturated pixels in the first image are replaced with data values for the corresponding pixels in the second image, with the data values for the replacing pixels (from the second image) increased or adjusted upwardly by the intensity ratio (obtained at step 224). At step 228, the first image having substituted pixels represents the ultimate final image of the sample, with a full dynamic range of light intensities, from the lowest intensity signals to the highest intensities signals at or near saturation.

It should be noted that, although a full dynamic range is now represented by the pixel data values in the final image, the final image may need to be scaled down, depending on the preferred data size for pixels in the imaging system. For example, in one embodiment, the actual data size used by the system for pixel values is sixteen bits (each pixel is represented by one value in a range of data values from 0 to 65,535). If the final image at step 228 has pixel values greater than that, then the entire image (the data value for each pixel) is scaled down so that every pixel has a value within the sixteen bit range of values (and the highest value pixels are no higher than a value of 65,535).

Figure 3:
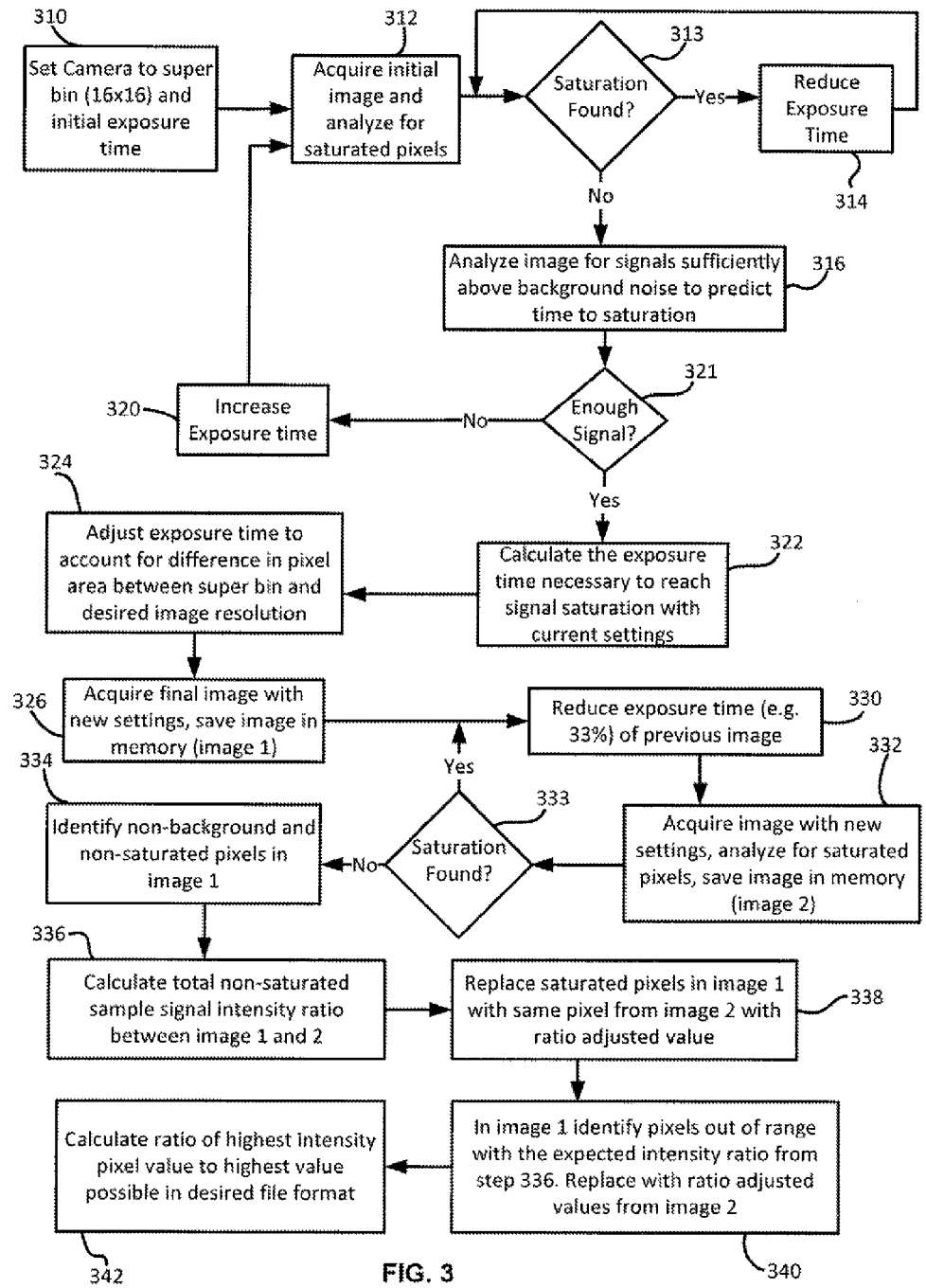
FIG. 3 illustrates a flow diagram of a process, in accordance with another embodiment, for calculating an exposure time and obtaining an image of detected chemiluminescence using the imaging system of FIG. 1.

A more specific and detailed implementation of a process, in accordance with another embodiment, for calculating the exposure time and obtaining a final image of a chemiluminescent sample is seen in FIG. 3.

At step 310, the CCD camera 120 is set (e.g., by the image processor 132) to a "super" or highly binned value in order to acquire an initial image. In the described embodiment, the binned value is 16×16 (256 pixel elements combined into each image pixel). Also, the camera is set to an initial exposure time established by the user. The initial exposure time could be based on the judgment or experience of the user so that the highest intensity signals in the initial image will be near saturation. However, as will be understood as this description progresses, there is variance permitted in establishing this binning value since the system will essentially correct the initial exposure with several quick (short exposure) follow-up images if the estimated time of exposure is not entirely suitable.

At step 312 an initial image is acquired and that image is analyzed for saturated pixels. Commercially available CCD cameras provide specifications with values for saturated pixels, and the processor 132 locates saturated pixels by comparing the pixel values in the initial image to the specified pixel saturation value. If pixels are found to be saturated (step 313), then the exposure time is reduced at step 314, and another image is acquired (repeating step 312), until an image is acquired that does not have saturation. Also, as mentioned earlier in connection with FIG. 2 (but not shown in FIG. 3), an additional displaced initial image may be acquired to detect higher intensity signals that straddle two adjacent binned pixels (see step 212).

Once there is no saturation, then at step 316 the resulting initial image (with no saturation) is evaluated to make sure that the signals captured at the pixels in the image are sufficiently above noise level to be meaningful in predicting the exposure time to reach saturation. The parameters for establishing if pixels are sufficiently above noise level can be based on the design of the camera and the system 100, but in one implementation, this condition is satisfied if at least 0.1% of the pixels in the image are at least 12.5% of the full dynamic range of the camera 120. If the signals are not sufficient (step 321), then the exposure time is increased at step 320, and steps 312, 314 and 316 are repeated.

If the signals are determined to be sufficiently above noise level (step 321), then the exposure time to reach saturation is calculated at step 322. It should be understood that the final image may be derived from several final images, and that the binning for the final image will be much lower (in order to achieve a higher resolution) than the binning set at step 310 for the initial image. As described earlier in conjunction with FIG. 2, in one embodiment, exposure time calculated at step 322 can be based on both a multiplying factor (that would bring the highest intensity signals in the initial image to saturation) and a pixel ratio reflecting the different binning values used in the initial images and the final image. The exposure time of the initial image is then adjusted at step 324 to take into account these two factors.

At least two final images are acquired in order to obtain a single final image reflecting the chemiluminescence of the sample 110. At step 326, a first final image is captured using the setting established at step 322, and saved into memory for further processing. Then, at step 330, the exposure time is reduced and a second final image is captured at step 332. The reduced exposure time for the second final image in the described embodiment is 67% less than the first final image, although the actual reduction could vary depending on the judgment and experiences of the user as well as the design of camera 120 and system 100. Also at step 332, the second image is analyzed for saturated pixels. If any saturated pixels in the second image are found (step 333), then steps 330 and 332 are repeated (with a decremented lower exposure time) until there are no saturated pixels found in the image. If no saturated pixels are found at step 333, then the process proceeds to step 334.

At step 334, pixels that are not background and not saturated pixels in the first image are identified. Non-background pixels will be those pixels having values above the bias or noise level established for the camera. In one embodiment, non-background pixels will be identified as any pixels within 2.5 standard deviations of the bias or inherent noise level established for the camera. At step 336, the intensity ratio between the non-background, non-saturated pixels identified in the first image at step 334 are compared to the corresponding pixels in the second final image in order to calculate an intensity ratio (as described earlier, the ratio that would be needed to bring the intensity of the pixels in the second image to the same level as the corresponding pixels in the first image).

At step 338, the saturated pixels in the first image are replaced with the same (corresponding) pixels of the second image, with the replacing pixels adjusted up by the intensity ratio calculated at step 336. At step 340, if after adjustment at step 338 there are other pixels (i.e., the pixels that were not replaced at step 338) in the first image going out of range (i.e., having values not in agreement with the value of the corresponding pixel in the second image), then those pixels may also be replaced with pixels from the second image, adjusted by the intensity ratio calculated at step 336. This step permits spurious pixels or signals, resulting from random factors such as cosmic rays, to be corrected. In one implementation, pixels in the first image are deemed out of range (not in agreement with the corresponding pixel in the second image) if they have more than a 10% variance from what would be expected by comparing the pixel in the first image to the corresponding pixel in the second image (with the pixel in the second image adjusted up by the intensity ratio calculated in step 336).

Finally, at step 342 all the pixel values in the final image are adjusted to the file format to be used by the imaging system and displayed at the user reporting system 150. For example, if the imaging system uses a 16 bit file, then all the pixel values in the final image will be adjusted (scaled down) so that the maximum value for any pixel will not exceed the value 65,535 for the 16 bit file.

It should be noted that, while not illustrated in FIG. 3, after a proper final image is obtained, conventional flat field correction may be used to compensate for normal optical distortions. If the results of the flat field correction results in any pixels being saturated (exceeding the maximum data value of pixels in the imaging system), the entire image may be ratio adjusted (scaled down). For example, if the data size used by the system for pixel values is sixteen bits (each pixel is represented by one value in the range from 0 to 65,535), then the entire image (each pixel) is be scaled down so that every pixel has a value within the sixteen bit range of values.

Figure 4:
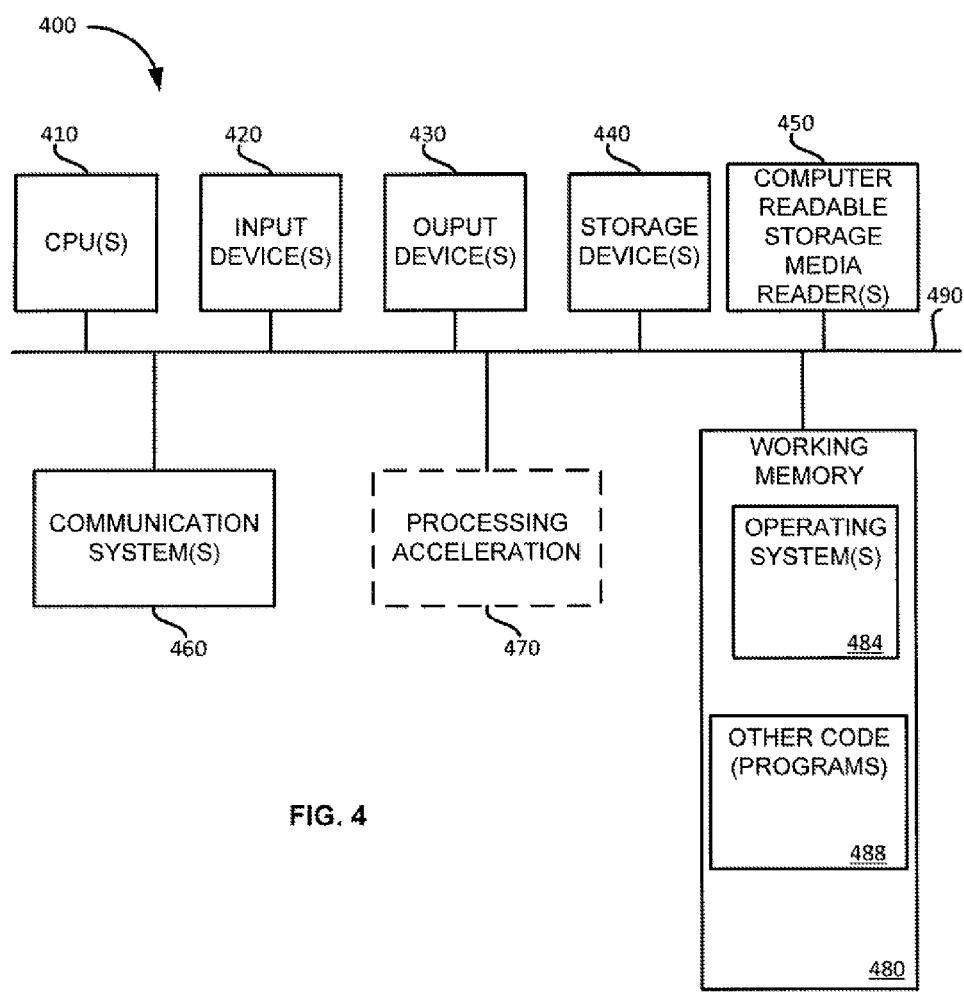
FIG. 4 is a block diagram illustrating an exemplary computer system upon which embodiments of the present invention may be implemented.

FIG. 4 is a block diagram illustrating an exemplary computer system upon which embodiments of the present invention may be implemented. This example illustrates a computer system 400 such as may be used, in whole, in part, or with various modifications, to provide the functions of the image processing system 130 and the user reporting system 150, as well as other components and functions of the invention described herein.

The computer system 400 is shown comprising hardware elements that may be electrically coupled via a bus 490. The hardware elements may include one or more central processing units 410, one or more input devices 420 (e.g., a mouse, a keyboard, etc.), and one or more output devices 430 (e.g., a display device, a printer, etc.). The computer system 400 may also include one or more storage devices 440, representing remote, local, fixed, and/or removable storage devices and storage media for temporarily and/or more permanently containing computer-readable information, and one or more storage media reader(s) 450 for accessing the storage device(s) 440. By way of example, storage device(s) 440 may be disk drives, optical storage devices, solid-state storage device such as a random access memory ("RAM") and/or a read-only memory ("ROM"), which can be programmable, flash-updateable or the like.

The computer system 400 may additionally include a communications system 460 (e.g., a modem, a network card—wireless or wired, an infra-red communication device, a Bluetooth™ device, a near field communications (NFC) device, a cellular communication device, etc.). The communications system 460 may permit data to be exchanged with a network, system, computer, mobile device and/or other component as described earlier. The system 400 also includes working memory 480, which may include RAM and ROM devices as described above. In some embodiments, the computer system 400 may also include a processing acceleration unit 470, which can include a digital signal processor, a special-purpose processor and/or the like.

The computer system 400 may also comprise software elements, shown as being located within a working memory 480, including an operating system 484 and/or other code 488. Software code 488 may be used for implementing functions of various elements of the architecture as described herein. For example, software stored on and/or executed by a computer system, such as system 400, can be used in implementing the processes seen in FIGS. 2 and 3.

It should be appreciated that alternative embodiments of a computer system 400 may have numerous variations from that described above. For example, customized hardware might also be used and/or particular elements might be implemented in hardware, software (including portable software, such as applets), or both. Furthermore, there may be connection to other computing devices such as network input/output and data acquisition devices (not shown).

While various methods and processes described herein may be described with respect to particular structural and/or functional components for ease of description, methods of the invention are not limited to any particular structural and/or functional architecture but instead can be implemented on any suitable hardware, firmware, and/or software configuration. Similarly, while various functionalities are ascribed to certain individual system components, unless the context dictates otherwise, this functionality can be distributed or combined among various other system components in accordance with different embodiments of the invention. As one example, the image processing system 130 may be implemented by a single system having one or more storage device and processing elements. As another example, the image processing system 130 may be implemented by plural systems, with their respective functions distributed across different systems either in one location or across a plurality of linked locations.

Moreover, while the various flows and processes described herein (e.g., those illustrated in FIGS. 2 and 3) are described in a particular order for ease of description, unless the context dictates otherwise, various procedures may be reordered, added, and/or omitted in accordance with various embodiments of the invention. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments may be described with (or without) certain features for ease of description and to illustrate exemplary features, the various components and/or features described herein with respect to a particular embodiment can be substituted, added, and/or subtracted to provide other embodiments, unless the context dictates otherwise. Further, the term "exemplary" used herein does not mean that the described example is preferred or better than other examples.

Consequently, although the invention has been described with respect to exemplary embodiments, it will be appreciated that the invention is intended to cover all modifications and equivalents within the scope of the following claims.

What is claimed is:

1. A method for measuring the chemiluminescence of a sample, comprising:
    acquiring a binned initial image of the sample, the initial image having a first binning value representing the number of pixel elements in its image pixels;
    calculating an exposure time for a final image of the sample, the final image having a second binning value representing the number of pixel elements in its image pixels, wherein the first binning value is larger than the second binning value, and wherein the calculation is based on a pixel ratio of the first binning value to the second binning value;
    acquiring at least first and second final images of the sample, wherein the first final image is acquired using the calculated exposure time, wherein the second final image is acquired using an exposure time shorter than the calculated exposure time;
    identifying pixels in the first final image that are saturated;
    measuring the intensity of luminescence of corresponding features in both the first and second final images, wherein measuring provides an intensity ratio that reflects the intensity of features in the first final image in relation to the intensity of the corresponding features in the second final image;
    substituting, for any saturated pixels in the first final image, corresponding pixels from the second final image; and
    adjusting the intensity of the corresponding pixels that are substituted for saturated pixels according to the intensity ratio.

2. The method of claim 1, further comprising:
    acquiring a second binned initial image of the sample, wherein the second initial image has its position shifted relative to the sample; and
    determining if the light intensity of binned pixels is higher in the second initial image;
    wherein the step of calculating an exposure time for a final image uses the one of the first and second initial images having a higher light intensity.

3. The method of claim 1, further comprising:
    determining if any pixels in the initial image are saturated; and
    if any of the pixels in the initial image are saturated, acquiring a second binned initial image of the sample with a shorter exposure time, and using the second initial image as the initial image in the step of calculating an exposure time for a final image of the sample.

4. The method of claim 1, further comprising:
    identifying the pixels in the initial image having the highest light intensity; and
    calculating a multiplying factor that would bring the identified image pixels to saturation;
    wherein the step of calculating an exposure time for the final image is further based on the multiplying factor.

5. The method of claim 4, wherein calculating an exposure time for the final image based on a pixel ratio comprises multiplying an exposure time of the initial image by the pixel ratio, and wherein calculating an exposure time for the final image based on the multiplying factor comprises additionally multiplying the exposure time of the initial image by the multiplying factor.

6. The method of claim 1, wherein the initial image comprises a first initial image, and wherein the method further comprises:
    determining if a predetermined number of pixels in the first initial image are above a predetermined noise level; and
    if a predetermined number of pixels are not above the predetermined noise level, acquiring a second initial image with a longer exposure time than the first initial image, and using the second initial image in the step of calculating an exposure time for a final image of the sample.

7. The method of claim 6, wherein the predetermined number of pixels is at least approximately 0.1% of pixels in the first initial image, and wherein the predetermined noise level is at least approximately 12.5% of the full dynamic range of a camera used to acquire the first initial image.

8. The method of claim 1, wherein the corresponding features comprise non-background and non-saturated pixels.

9. The method of claim 1, wherein the step of acquiring a binned initial image and the step of acquiring at least first and second final images are performed with the use of a charge coupled device.

10. A method for measuring the chemiluminescence of a sample, comprising:
   acquiring a binned, low resolution initial image of the sample;
   calculating an estimated exposure time for a final image of the sample, the final image having a higher resolution than the initial image, with the calculation based on the pixel ratio of the binned initial image to the final image;
   acquiring at least first and second final images of the sample, wherein the first final image is acquired using the calculated exposure time, wherein the second final image is acquired using an exposure time shorter than the calculated exposure time;
   identifying pixels in the first final image that are saturated;
   measuring the intensity of luminescence of corresponding features in both the first and second final images, wherein the features do not include pixels identified as saturated, and wherein the measuring is used to provide an intensity ratio that reflects the intensity of features in the first final image in relation to the intensity of the corresponding features in the second final image;
   substituting, for any identified saturated pixel in the first final image, a corresponding pixel from the second final image; and
   adjusting the intensity of the corresponding pixels that are substituted for saturated pixels according to the intensity ratio.

11. A method for detecting the chemiluminescence of a sample, comprising:
   determining an estimated exposure time for an image of the sample;
   acquiring at least first and second images of the sample, wherein the first image is acquired using the calculated exposure time, wherein the second image is acquired using an exposure time shorter than the calculated exposure time;
   identifying pixels in the first image that are saturated;
   measuring the intensity of luminescence of corresponding image features in both the first and second images, wherein the features do not include pixels identified as saturated, and wherein the measurement reflects an intensity ratio of the intensity of features in the first image in relation to the intensity of the corresponding features in the second image;
   substituting for any identified saturated pixel in the first image a corresponding pixel from the second image;
   adjusting, according to the intensity ratio, the intensity of the corresponding pixels in the second image that are substituted for identified saturated pixels in the first image; and
   providing the first image, with the adjusted substituted pixels from the second image, as the detected chemiluminescence of the sample.

12. A method for measuring the chemiluminescence of a sample using an image of the sample, comprising:
   acquiring at least a first, highly binned, initial image of the sample;
   determining if any pixels in the first initial image are saturated;
   if any pixels in the first initial image are saturated, acquiring a second, highly binned, initial image having a shorter exposure time;
   calculating an estimated exposure time for a higher resolution final image of the sample, based on (a) the pixel ratio of the first initial image binned image to the final image, if a second initial image has not been acquired or (b) the pixel ratio of the second initial binned image to the final image, if a second initial image has been acquired; and
   acquiring the final image of the sample using the calculated exposure time.

13. A system for measuring the chemiluminescence of a sample, comprising:
   a device for acquiring images of the sample;
   a processor; and
   a memory, the memory comprising a data storage area for storing instructions that are executable by the processor and that configure the system to:
   acquire a binned initial image of the sample, the initial image having a first binning value representing the number of pixel elements in its image pixels;
   calculate an exposure time for a final image of the sample, the final image having a second binning value representing the number of pixel elements in its image pixels, wherein the first binning value is larger than the second binning value, and wherein the calculation is based on a pixel ratio of the first binning to the second binning value;
   acquire at least first and second final images of the sample, wherein the first final image is acquired using the calculated exposure time, wherein the second final image is acquired using an exposure time shorter than the calculated exposure time;
   identify pixels in the first final image that are saturated;
   measure the intensity of luminescence of corresponding features in both the first and second final images, wherein the measurement provides an intensity ratio that reflects the intensity of features in the first final image in relation to the intensity of the corresponding features in the second final image;
   substitute, for any saturated pixels in the first final image, corresponding pixels from the second final image; and
   adjust the intensity of the corresponding pixels that are substituted for saturated pixels according to the intensity ratio.

14. The system of claim 13, wherein the instructions further configure the system to:
   acquire a second binned initial image of the sample, wherein the second initial image has its position shifted relative to the sample; and
   determine if the light intensity of binned pixels is higher in the second initial image;
   wherein the calculation of an exposure time for a final image uses the one of the first and second initial images having a higher light intensity.

15. The system of claim 13, wherein the instructions further configure the system to:
   determine if any pixels in the initial image are saturated; and
   if any of the pixels in the initial image are saturated, acquire a second binned initial image of the sample with a shorter exposure time, and use the second initial image as the initial image in order to calculate an exposure time for a final image of the sample.

16. The system of claim 13, wherein the instructions further configure the system to:

identify the pixels in the initial image having the highest light intensity; and calculate a multiplying factor that would bring the identified pixels to saturation;

wherein the calculation of an exposure time for the final image is further based on the multiplying factor.

17. The system of claim 16, wherein the calculation of an exposure time for the final image based on a pixel ratio comprises multiplying an exposure time of the initial image by the pixel ratio, and wherein the calculation of an exposure time for the final image based on the multiplying factor comprises additionally multiplying the exposure time of the initial image by the multiplying factor.

18. The system of claim 13, wherein the initial image comprises a first initial image, and wherein the instructions further configure the system to:

determine if a predetermined number of pixels in the first initial image are above a predetermined noise level; and if a predetermined number of pixels are not above the predetermined noise level, acquire a second initial image with a longer exposure time than the first initial image, and use the second initial image in the step of calculating an exposure time for a final image of the sample.

19. The system of claim 18, wherein the predetermined number of pixels is at least approximately 0.1% of pixels in the first initial image, and wherein the predetermined noise level is at least approximately 12.5% of the full dynamic range of a camera used to acquire the first initial image.

20. The system of claim 13, wherein the corresponding features comprise non-background and non-saturated pixels.

21. The system of claim 13, wherein the device for acquiring images comprises a charge coupled device.

* * * * *